United States Patent [19]

Mahood

[11] Patent Number: 5,561,181
[45] Date of Patent: Oct. 1, 1996

[54] ULTRA HIGH ORTHO NONYL PHENYL PHOSPHITE AND RESIN COMPOSITIONS STABILIZED THEREWITH

[75] Inventor: James A. Mahood, Morgantown, W. Va.

[73] Assignee: General Electric Company, Pittsfield, Mass.

[21] Appl. No.: 340,674

[22] Filed: Nov. 16, 1994

[51] Int. Cl.$^6$ ................................................ C08K 5/526
[52] U.S. Cl. ............................. 524/151; 558/95; 558/218
[58] Field of Search ...................... 558/95, 218; 560/780; 524/151

[56] References Cited

U.S. PATENT DOCUMENTS

| | | | |
|---|---|---|---|
| 2,733,226 | 1/1956 | Hunter | 524/151 |
| 3,305,520 | 2/1967 | Fritz et al. | 524/151 |
| 3,514,506 | 5/1970 | Wright | 558/95 |
| 5,254,709 | 10/1993 | Hunter | 558/95 |

FOREIGN PATENT DOCUMENTS 2039282  8/1980  United Kingdom.

*Primary Examiner*—Veronica P. Hoke

[57] ABSTRACT

An ultra high ortho nonyl phenol phosphite is provided in the form of a mixed ortho-para tris nonyl phenyl phosphite composition. The composition is produced by reacting $PCl_3$ with a nonyl phenyl composition comprising (a) para-unsubstituted/ortho substituted nonyl phenol present at a level of from 98 to 99.95 percent by weight based on the total weight of the nonyl phenol composition. The phosphite composition surprisingly and unexpectedly exhibits a substantial increase hydrolyric stability over that of conventional high ortho tris nonyl phenyl phosphite. The phosphite is useful for stabilizing thermoplastic compositions, which may be then extruded or molded into articles such as film, sheet or useful thermoplastic objects.

14 Claims, No Drawings

ULTRA HIGH ORTHO NONYL PHENYL PHOSPHITE AND RESIN COMPOSITIONS STABILIZED THEREWITH

BACKGROUND OF THE INVENTION

1. Field of the Invention

The present invention relates to phosphites, more particularly relates to alkyl aryl phosphites and thermoplastic compositions stabilized therewith.

2. Description of the Related Art

High ortho alkyl aryl phosphites and thermoplastic compositions stabilized therewith have been disclosed in Great Britain Patent 2039282. Generally, commercial tris nonyl phenyl phosphite (TNPP) compositions have had ortho levels of approximately 5 to 10 percent and para levels of between 90 and 95 percent. The Great Britain Patent 2039282 discloses TNPP compositions on Table 2 having ortho levels of 88 percent and para levels of 11 percent, and in Example 5 sets out TNPP having an ortho level of 88 percent. Page 1 of the reference on line 51 sets out the levels being at least 85 percent ortho. One problem with prior attempts to make unsubstituted para-ortho nonyl phenyl phosphites has been the difficulty in obtaining high purity para unsubstituted-ortho nonyl phenol. Due to the difficulty of obtaining such high purity material, prior attempts have utilized substituted para position ortho nonyl phenols in order to enhance the purity of the ortho position. Note that in the Great Britain Patent 2039282 that in reference to the examples 7 to 10 that it sets out a purity level of 93 percent to 99 percent as being achievable, but note that the only example involving a nonyl phenol has a methyl substituted para position. In other words, there historically has been difficulty in obtaining ultra high purity ortho nonyl phenol which has an unsubstituted para position, and as a result prior high ortho nonyl phenols utilizing an unsubstituted para position have typically been limited to purity levels of, for example, those set out in Table 2 and Example 5 being an 88 percent purity level. Prior ortho substitution levels of 80 to 90 percent have generally resulted in increases in hydrolytic stability of some 30 to 50 percent over commercial TNPP grades (5–10 percent ortho levels), and while such phosphites have exhibited enhanced levels of hydrolytic stability, there is still a need for higher degrees of hydrolytic stability due to the vulnerability of such phosphites to hydrolytic instability under humid conditions.

SUMMARY OF THE INVENTION

The present invention involves an ultra high ortho nonyl phenyl phosphite having unsubstituted para positions, which surprisingly and unexpectedly has yielded a substantial increase in hydrolytic stability of the phosphite over high ortho TNPPs (80–90% ortho). Specifically the tris nonyl phenyl phosphite of the present invention has'less than 1 percent para substitution and greater than 98 percent ortho substitution with nonyl groups. While prior ortho substitution levels of 80–90 percent have generally resulted in increases in hydrolytic stability of some 30–50 percent over commercial TNPP (5–10 percent ortho levels), the present invention yields hydrolytic stability increases of over 600 percent over commercial TNPP. This dramatic increase achieved by increases in purity levels is surprising and unexpected. The phosphites herein are especially resistant to humid conditions compared to the commercially available TNPPs and the TNPPs of GB2039282, and are useful in stabilizing thermoplastic compositions, particularly polyolefin compositions, even more particularly polypropylene compositions.

DETAILED DESCRIPTION OF THE INVENTION

The phosphites of the present invention are a mixed ortho-para tris nonylphenyl phosphite composition comprising at least 98 percent (preferably at least 99.1) by weight of a phosphite of the formula:

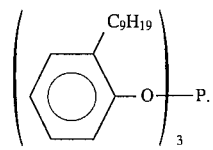

The phosphites are preferably made by reacting $PCl_3$ with a nonyl phenol composition comprising:

(a) para-unsubstituted/ortho substituted nonyl phenol present at a level of from 98 to 99.95 (preferably 99.1 to 99.95) percent by weight based on the total weight of the nonyl phenol composition. Preferably the nonyl phenol composition comprises from 99.2 to 99.9 percent by weight of a nonyl phenol of the formula

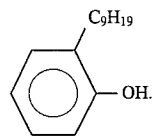

The mixed ortho-para tris nonyl phenyl phosphite compositions are useful in a stabilizing thermoplastic resin compositions, and are preferably present in the thermoplastic resin compositions at levels of from 10 parts per million (ppm) to 100 ppm based on the total weight of the thermoplastic composition. Preferably the thermoplastic composition comprises at least 95 percent by weight of a polyolefin. Preferably the polyolefin is polypropylene. The mixed ortho-para tris nonyl phenyl phosphite compositions of the present invention exhibit enhanced holydrolytic stability, and as set out above, surprisingly and unexpectedly exhibit a magnitude of order of enhancement in holydrolytic stability over high ortho TNPPs of GB2039282.

The present invention also involves a stabilized polymer compositions which includes an effective amount of the mixed phosphite composition described above. An amount of the phosphites of the invention is considered to be an "effective amount" when the polymer composition containing the phosphites of the invention shows improved stability in any of its physical or color properties in comparison to an analogous polymer composition which does not include a phosphite of the invention. In most polymer compositions, however, it will be preferred that the phosphites be present in an amount equal to about 0.01 to about 2 parts by weight per 100 parts by weight resin (phr). Amounts of about 0.01 to about 1 phr are more preferred, although most compositions will contain about 0.025 phr or more. The polymer composition may be thermoset in nature including unsaturated polyesters, phenolics, epoxy, urethanes, coating resins and crosslinkable latexes.

The polymer may also be any thermoplastic known in the art, such as polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Mixtures of different polymers, such as polyphenylene ether/styrenic resin blends, polyvinyl chloride/ABS or other impact modified polymers, such as methacrylonitrile and alphamethylstyrene containing ABS, and polyester/ABS or polycarbonate/ABS and polyester plus some other impact modifier may also be used. Such polymers are available commercially or may be made by means well known in the art. However, the phosphites of the invention are particularly useful in thermoplastic polymers, such as polyolefins, polycarbonates, polyesters, polyphenylene ethers and styrenic polymers, due to the extreme temperatures at which thermoplastic polymers are often processed and/or used. Recycled thermoplastics may also be used.

Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefines with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidenenorbornene; as well as mixtures of such copolymers and their mixtures with polymers mentioned above, for example polypropylene/ethylene propylene-copolymers, LDPE/EVA, LDPE/EAA, LLDPE/EVA and LLDPE/EAA.

Thermoplastic polymers may also include styrenic polymers, such as polystyrene, poly-(p-methylstyrene), poly-($\alpha$-methylstyrene), copolymers of styrene or $\alpha$-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate, styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene styrene. Styrenic polymers may additionally or alternatively include graft copolymers of styrene or alpha-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; sytrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/-propylene/diene terpolymers, styrene and acrylonitrile on polyacrylates or polymethacrylates, styrene and acrylonitrile on acrylate/butadiene copolymers, as well as mixtures of with the styrenic copolymers indicated above.

Nitrile polymers are also useful in the polymer composition of the invention. These include homopolymers and copolymers of acrylonitrile and its analogs, such as polymethacrylonitrile, polyacrylonitrile, acrylonitrile/-butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homo-and copolymers, polyvinyl chloride, polyvinyl bromide, polyvinyl fluoride, polyvinylidene chloride, chlorinated polyethylene, chlorinated polypropylene, florinated polyvinylidene, brominated polyethylene, chlorinated rubber, vinyl chloride-vinylacetate copolymers, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate tercopolymer, vinyl chloride-acrylic acid ester copolymers, vinyl chloride-maleic acid ester copolymers, vinyl chloride-methacrylic acid ester copolymers, vinyl chloride-acrylonitrile copolymer and internally platicized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4-dimethylol-cyclohexaneterephthalate, poly-2(2,2,4(4-hydroxyphenyl)-propane) terephthalate and polyhydroxybenzoates as well as block-copolyetheresters derived from polyethers having hydroxyl end groups.

Polyamides and copolyamides which are derived from diamines and dicarboxylic acids and/or from aminocarboxylic acids or the corresponding lactams, such as polyamide, 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifier, for example poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

The resulting stabilized polymer compositions of the invention may optionally also contain various conventional additives, such as the following:

1. Antioxidants 1.1 Alkylated monophenols, for example: 2,6 -di-tert-butyl-4-methylphenol, 2-tert-butyl-4,6 -dimethylphenol, 2,6-di-tert-butyl-4-ethylphenol, 2,6 -di-tert-butyl-4-n-butylphenol, 2,6-di-tert-butyl-4 -isobutylphenol, 2,6-dicyclopentyl-4-methylphenol, 2 -(alpha-methylcyclohexyl)-4,6 dimethylphenol, 2,6-dioctadecyl- 4-methylphenol, 2,4,6,-tricyclohexyphenol, 2,6-di-tert-butyl-4-methoxymethylphenol.

1.2 Alkylated hydroquinones, for example, 2,6 -di-tert-butyl-4-methoxyphenol, 2,5-di-tert-butyl-hydroquinone, 2,5-di-tert-amyl-hydroquinone, 2,6 -diphenyl-4octadecyloxyphenol.

1.3 Hydroxylated thiodiphenyl ethers, for example, 2,2'-thio-bis-(6-tert-butyl-4-methylphenol), 2,2'-thio-bis-(4-octylphenol), 4,4'thio-bis-(6-tert-butyl -3-methylphenol), 4,4'-thio-bis-(6-tert-butyl-2 -methyphenol).

1.4 Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(alpha-methylcyclohexyl)phenol), 2,2'-methylene-bis-(4-methyl-6-cyclohexylphenol), 2,2'-methylene-bis-(6-nonyl-4-methylphenol), 2,2'-methylene-bis-(6-nonyl-4 -methylphenol), 2,2'-methylene-bis-(6-(alpha-methylbenzyl)- 4-nonylphenol), 2,2'-methylene-bis-(6-(alpha,alpha-dimethylbenzyl)-4-nonyl-phenol). 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane. 2,6 -di-(3-tert-butyl-5-methyl-2-hydroxybenzyl)-4 -methylphenol, 1,1,3-tris-(5-tert-butyl-4-hydroxy-2 -methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene, di-(2-(3'-tert-butyl- 2'hydroxy-5'methylbenzyl)-6-tert-butyl-4 -methylphenyl)terephthalate.

1.5 Benzyl compounds, for example, 1,3,5-tris-(3,5-di-tert-butyl-4-hydroxybenzyl)-2,4,6 -trimethylbenzene, bis-(3,5-di-tert-butyl-4 -hydroxybenzyl)sulfide, isooctyl 3,5-di-tert-butyl-4 -hydroxybenzyl-mercapto-acetate, bis-(4-tert-butyl-3 -hydroxy-2,6-dimethylbenzyl)dithiol-terephthalate. 1,3,5-tris-(3,5-di-tert-butyl-4 hydroxybenzyl)isocyanurate. 1,3,5-tris-(4-tert-butyl- 3-hydroxy-2,6-dimethylbenzyl)isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris-(3,5 -dicyclohexyl-4-hydroxybenzyl)isocyanurate.

1.6 Acylaminophenols, for example, 4-hydroxylauric acid anilide, 4-hydroxy-stearic acid amilide, 2,4-bis-octylmercapto-6-(3,5-tert-butyl-4 -hydroxyanilino)-s-triazine, octyl-N-(3,5-di-tert-butyl- 4-hydroxyphenyl)-carbamate.

1.7 Esters of beta-(3,5-di-tert-butyl-4 -hydroxyphenol)-propionic acid with monohydric or polyhydric alcohols, for example, methanol, diethyleneglycol, octadecanol, triethyleneglycol, 1,6-hexanediol, penta-erythritol, neopentylglycol, tris-hydroxyethylisocyanurate, thiodiethyleneglycol, dihydroxyethyl oxalic acid diamide.

1.8 Esters of beta-(5-tert-butyl-4-hydroxy-3 -methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thidiethyleneglycol, dihydroxyethyl oxalic acid diamide.

1.9 Esters of beta-(5-tert-butyl-4-hydroxy-3 -methylphenyl) propionic acid with mono-or polyhydric alcohols, e.g., with methanol, diethylene glycol, octadecanol, triethylene glycol, 1,6-hexanediol, pentaerythritol, neopentyl glycol, tris(hydroxyethyl) isocyanurate, thiodiethylene glycol, N,N-bis(hydroxyethyl) oxalic acid diamide.

1.10 Amides of beta-(3,5-di-tert-butyl-4 -hydroxyphenol)-propionic acid for example, N,N'-di-(3,5-di-tert-butyl-4-hydroxyphenylpropionyl)-hexammethylen-diamine, N,N'-di-(3,5-di-tert-butyl-4 -hydroxyphenylpropionyl)trimethylenediamine, N,N'-di-(3,5-di-tert-butyl-4-hydroxyphenylpropionyl)-hydrazine.

2. UV absorbers and light stabilizers.

2.1 2-(2'-hydroxyphenyl)-benzotriazoles, for example, the 5'methyl-,3'5'-di-tert-butyl-,5'-tert-butyl-, 5'(1,1,3,3-tetramethylbutyl)-,5-chloro-3', 5'-di-tert-butyl-,5-chloro-3'tert-butyl-5'methyl-,3'sec -butyl-5'tert-butyl-,4'-octoxy,3', 5'-ditert-amyl- 3', 5'-bis-(alpha, alpha-dimethylbenzyl)-derivatives.

2.2 2-Hydroxy-benzophenones, for example, the 4-hydroxy-4-methoxy-,4-octoxy,4-decyloxy-,4 -dodecyloxy-,4-benzyloxy,4,2', 4'-trihydroxy-and 2'hydroxy-4,4'-dimethoxy derivative.

2.3 Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butylphenyl-3,5 -di-tert-butyl-4-hydroxybenzoate and hexadecyl-3,5-di-tert-butyl-4-hydroxybenzoate.

2.4 Acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)- 2-methylindoline.

2.5 Nickel compounds, for example, nickel complexes of 2, 2'-thio-bis(4-(1,1,1,3 -tetramethylbutyl)-phenol), such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands.

2.6 Sterically hindered amines, for example bis(2,2,6,6-tetramethylpiperidyl)-sebacate, bis-(1,2,2,6,6 -pentamethylpiperidyl)-sebacate, n-butyl- 3,5-di-tert-butyl-4-hydroxybenzyl malonic acid bis(1,2,2,6,6, -pentamethylpiperidyl) ester, condensation product of 1-hydroxyethyl-2,2,6,6 -tetramethyl-4-hydroxy-piperidine and succinic acid, condensation product of N,N'-(2,2,6,6-tetramethylpiperidyl)-hexamethylendiamine and 4-tert-octylamino- 2,6-dichloro-1,3,5-s-triazine, tris-( 2,2,6,6-tetramethylpiperidyl)-nitrilotriacetate, tetrakis-(2,2,6,6-tetramethyl-4-piperidyl)-1, 2,3,4 -butane-tetra-carbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4 -yl)sebacate: 1-hydroxy 2,2,6,6-tetramethyl-4 -benzoxypiperidine; 1-hydroxy-2,2,6,6-tetramethyl-4 -(3,5-di-tert-butyl-4-hydroxy hydrocinnamoyloxy)-piperdine; and N-(1-hydroxy-2,2,6,6-tetramethyl-piperidin- 4-71)-epsiloncaprolactam.

2.7 Oxalic acid diamides, for examples, 4,4'-dioctyloxy-oxanilide, 2,2'-di-octyloxy-5',5'-di-tert-butyloxanilide, 2,2'-di-dodecyloxy-5',5'di-tert-butyl-oxanilide, 2-ethoxy-2'-ethyl-oxanilide, N,N'-bis(3-dimethylaminopropyl)-oxalamide, 2-ethoxy-5 -tert-butyl-2'-ethyloxanilide and its mixture with 2 -ethoxy-2'ethyl-5,4-di-tert-butyloxanilide and mixtures of ortho-and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tris(nonyl-phenyl)phosphite, trilauryl phosphite, triocta-decyl phosphite, distearyl pentaerythritol diphosphite, tris(2, 4-di-tert-butylphenyl)phosphite, diisodecyl pentaerythritol diphosphite, bis(2,4-di-tert-butylphenyl)pentaerythritol diphosphite tristearyl sorbitol triphosphite, and tetrakis(2,4-di-tert-butylphenyl) 4,4'-biphenylene diphosphonite.

5. Peroxide scavengers, for example, esters of betathiodipropionic acid, for example the lauryl, stearyl, myristyl or tridecyl esters, mercaptobenzimidazole or the zinc salt of 2 -mercaptobenzimidazole, zinc-dibutyldithiocaramate, dioctadecyldisulfide, pentaerythritoltetrakis-(beta-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, calcium stearoyl lactate, calcium lactate, Zn stearate, Mg stearate, Na ricinoleate and K palmirate, antimony pyrocatecholate or zinc pyrocatecholate.

8. Nucleating agents, for example, metal salts of 4-tert butylbenzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black and graphite.

10. The present invention may also be used in conjunction with aminoxy propanoate derivatives such as methyl-3-(N, N-dibenzylaminoxy)propanoate; ethyl-3 -(N,N-dibenzylaminoxy) propanonoate; 1,6-hexamethylene-bis( 3-N,N-dibenzylaminoxy)proponoate); methyl-(2 -(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

11. Other additives, for example, plasticizers, lubricants, emulsifiers, pigments, optical brighteners, flameproofing agents, anti -static agents, blowing agents and thiosynergists such as dilaurythiodipropionate or distearylthiodipropionate.

EXAMPLES

TABLE 1

| Ex. | Phos. | Time (Hrs) |
|---|---|---|
| A | TNPP (5–10) | 34 |
| 1 | UHTNPP | 225 |

TABLE 2

| B | TNPP (5–10) | 44 |
|---|---|---|
| C | TNPP (90) | 53 |
| D | TNCP | 121 |

The ultra high ortho TNPP of Example 1 had greater than 98% ortho with the para position unsubstituted, and it is believed that it was greater than 99% ortho. The TNPP (5–10) was conventional TNPP having 5–10% ortho TNPP. The TNPP (90) was high ortho (90% ortho) TNPP. The TNCP was a 98+% ortho nonyl having the para position substituted with cresol (in other words, ortho-nonyl-para-cresol was used in place of ortho nonyl phenol. Table 1 involved time in hours to 1% weight gain for the phosphites at room temperature and a 75% nominal relative humidity. Table 2 involved time in hours to 1% weight gain for the phosphite at 30° C. and 87% nominal relative humidity. Note the unexpectedly superior resistance to weight gain evidenced by the ultra high ortho TNPP (UHTNPP) over the comparative examples.

I claim:

1. A mixed ortho-para tris nonyl phenyl phosphite composition produced by reacting $PCl_3$ with a nonyl phenol composition comprising (a) para-unsubstituted/ortho substituted nonyl phenol present at a level of from 98 to 99.95 percent by weight based on the total weight of the nonyl phenol composition.

2. The phosphite composition of claim 1 wherein said nonyl phenol composition comprises from 99.2 to 99.9 percent by weight of a nonyl phenol of the formula:

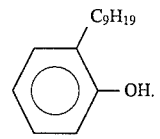

3. A mixed ortho-para tris nonyl phenyl phosphite composition comprising at least 98 percent by weight of a phosphite of the formula:

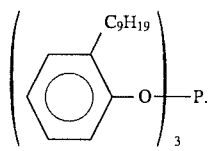

4. A thermoplastic resin composition comprising from 100 ppm to 1000 ppm of the phosphite composition of claim 1.

5. A thermoplastic resin composition comprising from 100 ppm to 1000 ppm of the phosphite composition of claim 2.

6. A thermoplastic resin composition comprising from 100 ppm to 1000 ppm of the phosphite composition of claim 3.

7. The resin composition of claim 4 wherein said resin composition comprises at least 95 percent by weight polyolefin.

8. The resin composition of claim 5 wherein said resin composition comprises at least 95 percent by weight polyolefin.

9. The resin composition of claim 6 wherein said resin composition comprises at least 95 percent by weight polyolefin.

10. The resin composition of claim 7 wherein said polyolefin is polypropylene.

11. The resin composition of claim 8 wherein said polyolefin is polypropylene.

12. The resin composition of claim 9 wherein said polyolefin is polypropylene.

13. The phosphite of claim 1 wherein para-unsubstituted/ortho substituted nonyl phenol is present at a level of from 99.1 to 99.95 percent by weight based on the total weight of the nonyl phenol composition.

14. The phosphite of claim 3 wherein phosphite of the formula is present at a level of at least 99.1 percent by weight based on the total weight of the composition.

* * * * *